United States Patent [19]

Takatsu

[11] Patent Number: 4,850,875
[45] Date of Patent: Jul. 25, 1989

[54] FILLING AND FORMING SYSTEM FOR DENTAL VISCOUS PLASTIC MATERIALS UTILIZING ULTRASONIC VIBRATION

[75] Inventor: Toshio Takatsu, No. 7-2-504, Tsudanuma 2-chome, Narashino-shi, Chiba-ken, Japan

[73] Assignees: Toshio Takatsu, Narashino; G-C Dental Industrial Corp., Tokyo, both of Japan

[21] Appl. No.: 140,994

[22] Filed: Jan. 5, 1988

[30] Foreign Application Priority Data

Jan. 26, 1987 [JP]  Japan ................................. 62-14279

[51] Int. Cl.⁴ .............................................. A61C 5/04
[52] U.S. Cl. ................................... 433/226; 433/164; 433/119; 433/215
[58] Field of Search ............... 433/215, 226, 119, 164, 433/118

[56] References Cited

U.S. PATENT DOCUMENTS 3,898,739  8/1975  Gayso ................................. 433/118
4,634,383  1/1987  Beyer et al. ......................... 433/164

FOREIGN PATENT DOCUMENTS 2755515  6/1979  Fed. Rep. of Germany ...... 433/118

Primary Examiner—John J. Wilson
Attorney, Agent, or Firm—Oblon, Spivak, McClelland, Maier & Neustadt

[57] ABSTRACT

A filling and forming system for dental viscous plastic materials utilizing ultrasonic vibrations in which a dental plastic material possessing viscousness (such as light polymerizable type composite resins) is used in the mouth cavity. Generation of ultrasonic vibrations from the tip of a forming instrument and application thereof to a dental material are obtained without generating heat in the absence of poured water. The effect of the ultrasonic vibrations permits the prevention of the adhesion of the material to the instrument. Additionally, it decreases the consistency of the material, thus making the filling and forming of the material easy and enhancing the close adaptation of the material.

1 Claim, 1 Drawing Sheet

FILLING AND FORMING SYSTEM FOR DENTAL VISCOUS PLASTIC MATERIALS UTILIZING ULTRASONIC VIBRATION

BACKGROUND OF THE INVENTION

1. Field of the Invention

The present invention relates to a filling and forming method for dental viscous plastic materials such as composite resins. More particularly, it pertains to a method for dental treatments of high efficiency and high quality in a wide area of dentistry. The method involves the application of ultrasonic vibrations to the tips of filling or forming instruments. With the obtained fine vibration effect, it is possible to most effectively prevent the adhesion of the material to the instruments, which has been the gravest problem in operations, and to cause a decrease in the consistency of the material, thereby making the filling and forming of the material easy and, at the same time, improving the close adaptation of the material with respect to an application body.

2. Statement of the Prior Art

Referring typically to the tooth restoration with a composite resin, in which considerable weight is given to the aesthetical properties, filling and forming are very important steps. However, the operation for forming a resin material is troublesome, complicated, and hard to carry out. Therefore, a great deal of efforts have been devoted to simplifying this operation with enhanced efficiency. However, these efforts are limited to mere improvements in the form of the tip portions of forming instruments, and spatulashaped filling instruments are still frequently used. So far as is known by the present invention, an instrument having a vibrational function has not been used for this purpose. Although current instruments are formed of metals, plastics, etc., the resin material adheres to whatever forming instruments are used. Thus, difficulty experienced in forming still remains unsolved.

Fundamentally, the conventional methods for filling and forming dental viscous materials have several disadvantages, including:

(1) Adhesion of the material to forming instruments,
(2) Slip of the material on and along the body to which it is applied, and
(3) Deficiency in the close adaptation of the material to the body to which it is applied. However, these disadvantages have only been handled by makeshift means.

Reference will now be made to tooth restoration with a composite resin by way of example.

(1) Adhesion of Resin Material to Forming Instrument

The resin material adheres to a forming instrument which may be formed of a metal or plastics, or may be surface-treated with Teflon ®. Whenever the resin material adheres to the tip of the forming instrument, it has been wiped off by a cotton ball impregnated with an alcohol so as to repeatedly use that instrument for filling. This method is far from being satisfactory, partly because it involves a very troublesome operation and partly because it is likely that such a separating agent may cause the degradation of the nature of the resin, or may decrease the close adaptation and adhesion of the resin to the cavity wall.

(2) Slip of the Placed Resin on the Cavity Wall

In recent years, much use has been made of resins containing an increased amount of fillers and, hence, showing a high degree of consistency. Such resins are convenient, since they can easily be filled and formed in intra coronal cavities such as Class I or 2 cavities. In the case of wedge-shaped defect cavities or extensive Class 5 cavities, however, the resin material tends to slip on and along the cavity wall according to the movement of the instrument, and the resin is not always easy to handle. This is because the resin material is hard and poor in flowability. As a result, forming cannot be carried out until, after filling the resin into the cavities, the consistency thereof decreases with a temperature rising to such an extent that the resin material closely adheres more or less to the surface of the cavity wall owing to a slight increase in the flowability thereof. This is the present situation, and it incurs inconvenience. Under such a condition, since the resin may still tend to slip considerably on the cavity wall, some difficulty is still encountered in forming with a manual filling instrument.

(3) Deficiency in the Close Adapation of Resin Material to the Cavity Wall

When using a resin which has a low flowability, the resin tends to slip easily on the cavity wall, and it is apt to adhere to the forming instrument, and sufficient close adaptation of the resin material to a cavity wall is not achieveable by filling under pressure relying upon the manual instrument.

SUMMARY OF THE INVENTION

In order to remove the disadvantages the prior art possess, as mentioned above, without making any particular modification to the material or tip of the instrument or using any separate agent, the present inventor has invented a filling and forming method in which ultrasonic vibrations from the tip of a forming instrument are applied to a dental material. According to the present method, the adhesion of a resin material to the forming instrument can be thoroughly prevented by the repulsing effect of ultrasonic vibrations. Additionally, the consistency of the resin material is decreased by the thixotropic effect of fine ultrasonic vibrations, thereby improving the forming properties of the resin material and the close adaptation thereof to the cavity wall. Thus, the present invention provides a filling and forming system which can eliminate all the problems of the prior art, as already mentioned.

GENERAL DISCUSSION OF THE INVENTION

The filling and forming instruments used with the present system should possess the following properties:

(1) They can produce various outputs of ultrasonic vibrations, but should not generate any heat, even when used in the absence of poured water.

(2) They have their tip portions formed of not only a metal but also a plastic material, or formed of a surface-treated thick plastic material with a metallic core.

(3) Any ultrasonic waves generally used in dentistry may be applied (as well as others) may be used in the present invention.

Referring further to the above-mentioned item (2), if a metallic tip is used for the filling and forming of a composite resin, it may then wear away due to friction with the tooth surface or the fillers contained in that resin, resulting in blackening of that resin, or it emits a noticeable impact (sound) or give acute pain to a patient due to contact with the tooth substance. Hence, it is preferred that tips other than metallic tips are used for composite resins.

The present inventor has made a model of the aforesaid system, and applied it to a number of examples of the tooth restoration with light polymerizable type composite resins to examine its filling and forming properties. As a result, the adhesion of the resin material to the tip of the present model was hardly caused with a suitable decrease in the consistency of the resin material under the action of the ulrasonic vibrations generated therefrom, whereby the resin material could be filled and formed in the cavities in an extremely smooth manner. Thus, the effectiveness of the present system could be ascertained.

BRIEF DESCRIPTION OF THE DRAWINGS

The present system will additionally be explained with reference to the accompanying drawings, in which.

DETAILED DESCRIPTION OF THE PRESENTLY PREFERRED EMBODIMENT

Figure 1:
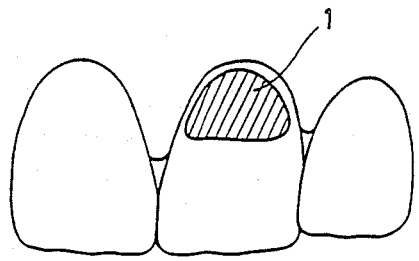
FIGS. 1 to 4 are labial views of examples in which the present system was applied to the restoration of cervical caries in the upper left laternal incisor of a patient with a light polymerizable type composite resin.
Figure 2:
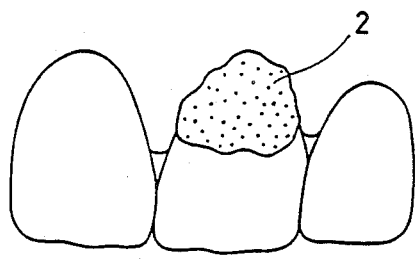
Figure 3:
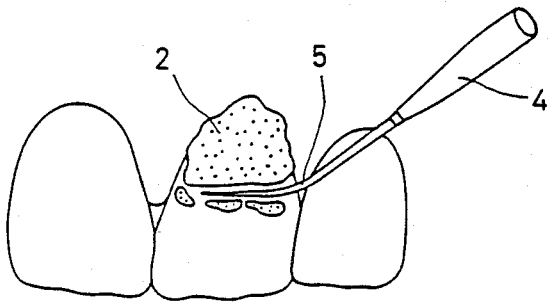
Figure 4:
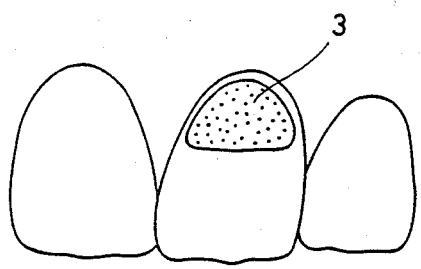

Referring to FIG. 1, the caries lesion is removed, and the Class 5 cavity (shown by a hatched region 1) is completed. In FIG. 2, a light polymerizable type composite resin is filled in the cavity, while applying ultrasonic vibrations to a test piece-forming instrument, and an over-filled resin portion still remains (shown by dots 2). Referring to FIG. 3, the resin material is formed, while generating ultrasonic vibrations and removing the over-filled resion portion from the incisal cavo-margin with a forming instrument (shown at 4) having a tip 5. The resin is smoothly cut out from the cavo-margin without adhering to the tip 5 of the forming instrument 4. Thus, the treatments are smoothly carried out without causing the ultrasonic vibrations to give impacts or pains to the patient. Referring to FIG. 4, the removal of the over-filled resin portion and the filling of the resin are also similarly finished on the cervial cavo-margin. The resin material adapts properly and closely to the whole cavity wall, while maintaining the proper form (shown at 3).

The present system is designed to be most frequently and effectively applied to tooth crown restoration with a light polymerizable type composite resin. Further, the present system is effectively applied to the field of conservative dentistry i.e. to filling and forming to be effected in the tooth crown restoration with a chemically polymerizable type composite resin or glass ionomer cement or filling and forming to be effected after cavity preparation or in temporary sealing with eugenol cement during endodontical treatment. Still further, the present system is effectively applicable to the field of prosthetic dentistry, i.e., to the filling and forming of a light or chemically polymerizable type composite resin in the veneer of a cast crown, to the removal of excessive resin placed on the plate margin, or to forming when a denture plate is rebased with a light polymerizable composite resin. Still further, the present system is effectively applicable to the field of preventive dentistry, when a resin or cement type pit and fissure sealant is used. Thus, the present system makes it possible to provide high-efficient and -quality treatments in a wide area of clinical dentistry.

What is claimed is

1. A method of dental restoration by filling and forming viscous dental plastics, said method comprising the steps of placing a viscous dental plastic in a patient's mouth in the region of the teeth to be restored, applying ultrasonic vibrations to said viscous dental plastic in situ while the viscous dental plastic is being formed and compacted with a forming instrument, thereby preventing adhesion of the viscous dental plastic to the forming instrument, decreasing the viscosity of the viscous dental plastic, and enhancing the close adaptation of the viscous dental plastic to its desired situs.

* * * * *